United States Patent

Mancosu et al.

Patent Number: 5,321,256
Date of Patent: Jun. 14, 1994

[54] PROCESS AND APPARATUS FOR INSPECTING JUNCTIONS IN SLEEVE LINING FABRICS FOR THE MANUFACTURE OF TOOTHED BELTS

[75] Inventors: Frederico Mancosu, Milan; Roberto Sgnaolin, Piovera; Roberto Zavaglio, Milan, all of Italy

[73] Assignee: Pirelli Prodotti Diversificati S.p.A., Milan, Italy

[21] Appl. No.: 793,732

[22] Filed: Nov. 21, 1991

[30] Foreign Application Priority Data

Nov. 21, 1990 [IT] Italy .................. 22125 A/90

[51] Int. Cl.⁵ .................. G01N 21/86; G01J 3/50
[52] U.S. Cl. .................. 250/226; 250/571; 209/580
[58] Field of Search ............ 250/226, 562, 571, 572; 209/580-582; 356/237, 424, 429, 430; 73/622

[56] References Cited

U.S. PATENT DOCUMENTS

| | | |
|---|---|---|
| 3,536,409 | 10/1970 | Belser. |
| 3,873,830 | 3/1975 | Forster .................. 250/226 |
| 3,898,469 | 8/1975 | Nichols et al. |
| 4,513,316 | 4/1985 | Kobayashi et al. .......... 356/237 |
| 4,567,372 | 1/1986 | Henry et al. .............. 250/560 |
| 4,850,943 | 7/1989 | DiGiacomo et al. .......... 474/205 |
| 5,150,175 | 9/1992 | Whitman et al. ............ 356/429 |
| 5,239,184 | 8/1993 | Mancosu et al. ............ 356/430 |
| 5,247,463 | 9/1993 | Mancuso et al. ............ 364/560 |

FOREIGN PATENT DOCUMENTS 0234492  9/1987  European Pat. Off.

*Primary Examiner*—David C. Nelms
*Assistant Examiner*—Stephone B. Allen
*Attorney, Agent, or Firm*—Stevens, Davis, Miller & Mosher

[57] ABSTRACT

A tubular sleeve (2) having a toothed inner surface (2a) is operatively mounted on rollers (12, 13) which rotate the sleeve (2) transversely to the extension of the teeth (5). photochromatic sensor (22) which is movable parallel to the rollers (12, 13) detects the presence of possible separation areas (9) between the sewn together end edges (6a, 6b) of a lining fabric (6) applied to the toothed surface (2a) of the sleeve (2), the end edges (6a, 6b) being chromatically differentiated from the elastomeric material (4) and from each other. An electronic processing unit (25) carries out the identification and storage of the position of the separation areas (9) detected by the photochromatic sensor (22). With the aid of a reading member (27) associated with the photochromatic sensor (22), the processing unit (25) identifies the position of the junction (7) between the end edges (6a, 6b) on the extension outline of the toothed surface (2a), in order to detect and store the presence of possible anomalous positionings of the junction itself.

22 Claims, 3 Drawing Sheets

PROCESS AND APPARATUS FOR INSPECTING JUNCTIONS IN SLEEVE LINING FABRICS FOR THE MANUFACTURE OF TOOTHED BELTS

CROSS REFERENCE TO RELATED APPLICATIONS

Copending U. S. application Ser. No. 07/792,879, filed on even date herewith and corresponding to: U.S. Pat. No. 5,198,068.

Italian Application 22 121 A/90, filed Nov. 21, 1990 for PROCESS AND APPARATUS TO APPLY IDENTIFICATION INSCRIPTIONS ON SLEEVES MADE OF ELASTOMERIC MATERIAL IN THE MANUFACTURE OF DRIVING BELTS (WAK 28335, case 9015);

Italian Application 22 123 A/90, filed Nov. 21, 1990 for PROCESS AND APPARATUS FOR HANDLING DRIVING BELTS IN AN AUTOMATED MANNER (WAK 28349, case 9017);

Italian Application 22 124 A/90, filed Nov. 21, 1990 for MACHINE AND PROCESS FOR COILING AND WINDING TUBULAR SLEEVES OF ELASTOMERIC MATERIAL INCORPORATING REINFORCING FIBERS (WAK 28350, case 9018);

Italian Application 22 126 A/90, filed Nov. 21, 1990 for PROCESS AND APPARATUS TO IDENTIFY THE PRESENCE OF STRUCTURAL CAVITIES IN SLEEVES FOR THE MANUFACTURE OF DRIVING BELTS (WAK 28710, case 9021);

Italian Application 22 127 A/90, filed Nov. 21, 1990 for PROCESS AND AUTOMATIC INSTALLATION FOR THE CONTROL OF THE QUALITY AND OF THE PRODUCTION OF TRANSMISSION BELTS (WAK 28352, case 9022);

Italian Application 22 128 A/90, filed Nov. 21, 1990 for A PROCESS AND APPARATUS FOR INSPECTING THE GEOMETRICAL CONFIGURATION OF TOOTHED DRIVING ELEMENTS (WAK 28351, case 9019).

The disclosure of each of the above identified U.S. and Italian Applications are hereby incorporated by reference.

BACKGROUND OF THE INVENTION

The present invention relates to a process and an apparatus for inspecting junctions in sleeve lining fabrics for the manufacture of toothed belts, each sleeve having a substantially cylindrical textile reinforcing layer embedded in at least one layer of elastomeric material shaped so as to define, in said sleeve, an toothed surface on its inner periphery provided with a number of shaped teeth extending parallel to the axis of the sleeve. The teeth are spaced apart from each other by a predetermined pitch, a fabric lining being applied to said toothed surface, said lining having at least two end edges joined by a seam extending longitudinally in the sleeve.

It is known that driving belts are essentially comprised of an inextensible textile layer of substantially cylindrical structure embedded in at least a layer of elastomeric material such shaped as to define a toothed inner surface. In many cases, a fabric lining is applied to the inner toothed surface and it has the double function of reinforcing the individual teeth by enhancing the bending strength thereof and protecting the elastomeric material from external agents with which the belt may be brought into contact, once it has been placed in use.

Belts of the above type are obtained from a slitting operation carried out according to a number of axially spaced circumferential lines on an axially elongated tubular cylindrical sleeve having a toothed inner surface.

For the manufacture of this sleeve a tubular body made of stretch fabric is first slipped onto a cylindrical matrix provided with longitudinal grooves the shape of which matches the shape of the teeth. This tubular body, designed to form said fabric lining, is substantially formed with one or more lengths of rubberized fabric the end edges of which are disposed close to each other and joined by at least one connecting seam extending longitudinally to the resulting tubular body.

Then at least one reinforcing layer of inextensible textile material is wrapped around the textile tubular body fitted on the matrix and at least one layer of uncured elastomeric material is subsequently placed over the reinforcing layer. The semifinished product thus obtained is submitted to a vulcanization process in an autoclave.

During this operation the semifinished product, after being engaged in a coating sheath made of rubber, undergoes a suitable heating by steam under pressure which is sent to the inside of the matrix and the outside of the sheath which surrounds the semifinished product.

By the effect of the steam pressure acting on said coating rubber sheath through homogeneously distributed centripetal forces the elastomeric material is forced to pass through the inextensible textile fibers so that it fills the grooves of the matrix thereby creating the inner toothing of the sleeve. During this step the part of the lining fabric which is impervious to the elastomeric material is pushed into the grooves and perfectly mates with the matrix surface.

Therefore when the vulcanization is over the lining fabric will be located directly on the inner surface of the finished sleeve and will be able to perform the above mentioned functions in the belts to be obtained from the sleeve by the circumferential slitting of the sleeve after removing the sleeve from the matrix.

As a result of the above process it is noted that the thrust action exerted by the elastomeric material during the vulcanization process in some cases can give rise to the separation from each other of the end edges of the lining fabric in the junction area.

It can be easily understood that such a detachment can give rise to the complete loss of operating features of the fabric lining. In fact external agents such as chemicals or other agents can easily damage the elastomeric material through any open junction areas, which can bring about a quick deterioration of the belt and the consequent breakage of it.

The presence of separation areas between the end edges of the fabric can also involve an unacceptable weakening of the bending strength of the tooth on which the junction is located.

It is also to be pointed out that in many applications the junction or junctions must have a predetermined positioning on the tooth outline. In fact if the junction is positioned at particular locations on the tooth outline, such as for example on one of the tooth flanks, it could give rise to an undesirable reduction in the resistance to bending stress of the tooth even if it has been correctly made.

In addition, under this situation the junction would be submitted to high stresses that could cause the separation of the fabric edges while the belt is being used.

It is apparent that the above described situations bring about high risks of breakage of the belt in use, which must be absolutely avoided.

The methods currently adopted in an attempt to restrain said risks as much as possible are essentially based on the performance of quality inspections carried out by an operator who merely visually observes the toothed surface of the sleeve or the belts subsequently obtained.

It can be easily understood that these empirical inspection methods are not very reliable, since the identification of possible anomalies in the lining fabric junctions depends to a great extent on the skill of the operator entrusted with this inspection and the care he or she takes in carrying out the operation.

In this connection it is also necessary to consider the fact that visual identification of possible separations between the seamed edges of the lining fabric is very difficult, since both the lining fabric and the elastomeric material appear generally black to the human eye.

In addition it must be born in mind that the inspection methods currently used do not allow timely interventions when the junctions have anomalies due to high speed running of the apparatus used during the sleeve manufacturing operations.

SUMMARY OF THE INVENTION

The main object of the present invention is substantially to solve the problems of the known art by a process and an apparatus enabling a precise and reliable inspection to be carried out on the junctions of the fabric lining in a sleeve.

Another object of the invention is to provide a process and an apparatus capable of identifying and timely signalling the presence of anomalies in the fabric lining junctions due to improper running of the apparatus used in the production processes for the manufacture of sleeves in order to enable immediate interventions for the elimination of said anomalies.

The foregoing and further objects that will become more apparent in the course of the following description are substantially attained by a process for inspecting junctions in sleeve lining fabrics for the manufacture of toothed belts, characterized in that it comprises the following steps:

a) operatively mounting the sleeve on supporting and motion-imparting means;

b) moving the sleeve transversely to its longitudinal axis;

c) positioning a photochromatic sensor before the inner toothed surface of the sleeve, said photochromatic sensor being arranged to emit variable electric signals depending on the color exhibited by the toothed surface at one reading point;

d) moving the photochromatic sensor according to a direction parallel to the sleeve axis, so that said first reading point helically translates relative to the sleeve axis;

e) detecting and recording the signals emitted by the photochromatic sensor when, due to the passage of said junction before the first reading point, a mutual separation between the joined fabric end edges is identified, said end edges being chromatically differentiated at least from the elastomeric material layer;

f) detecting and recording the photochromatic sensor's position along the longitudinal extension of the sleeve, when a separation area between the lining fabric end edges is identified at said junction.

In accordance with the invention, this process is put into practice by an apparatus for the inspection of junctions in sleeve in that it comprises:

supporting means arranged to operatively engage the sleeve;

first motion-imparting means cooperating with said supporting means to impart a continuous movement to the sleeve in a direction transversely to its longitudinal extension;

at least one photochromatic sensor acting on the toothed surface and arranged to emit variable electric signals depending upon the color exhibited by the toothed surface at one reading point;

second motion-imparting means acting on the photochromatic sensor to impart a translation motion to the sensor in a direction parallel to the sleeve axis, so that the first reading point translates helically to the sleeve axis;

an electronic processing unit operatively connected to the photochromatic sensor in order to identify the presence of mutual separation areas between said end edges of the fabric, as well as to the second motion-imparting means in order to identify the location of said separation areas on the longitudinal extension of the sleeve, said end edges being chromatically differentiated at least from said elastomeric layer.

BRIEF DESCRIPTION OF THE DRAWINGS

Further features and advantages will be best understood from the detailed description of a preferred embodiment of a process and an apparatus for the inspection of junctions in sleeve lining fabrics for the manufacture of toothed belts in accordance with the present invention, taken hereinafter by way of non-limiting example with reference to the accompanying drawings, in which.

DETAILED DESCRIPTION OF A PREFERRED EMBODIMENT

Figure 1:
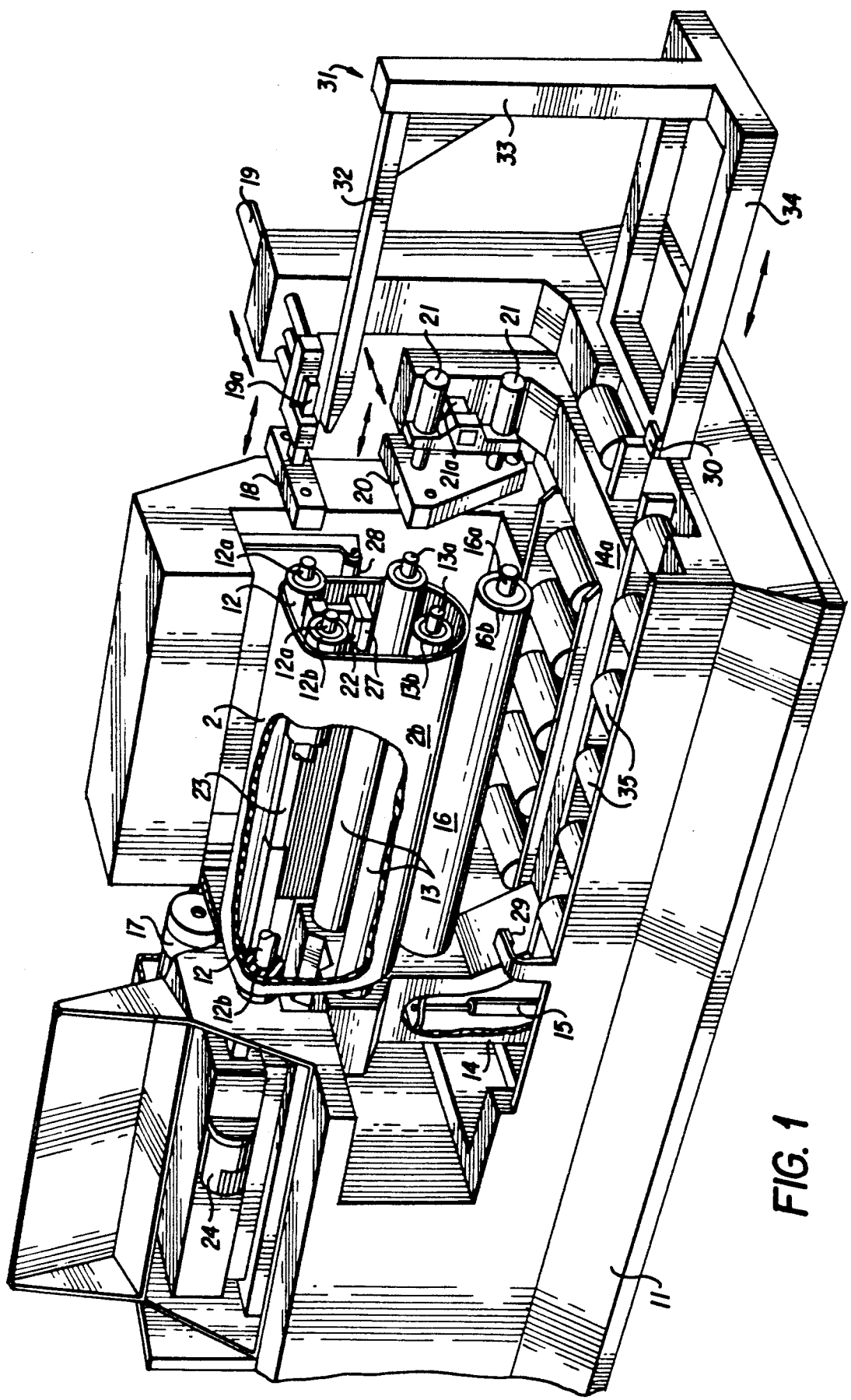
FIG. 1 is a perspective view of an apparatus used to put the process of the invention into practice in the manufacture of sleeves for producing toothed belts.

Referring to the drawings and in particular to FIG. 1, an apparatus for the inspection of junctions in sleeve lining fabrics for the manufacture of toothed belts in accordance with the invention has been generally identified by reference numeral 1.

Apparatus 1 is adapted to act on sleeves 2 of substantially cylindrical tubular configuration designed to subsequently undergo a slitting operation according to a plurality of circumferential lines for the manufacture of a number of toothed belts of predetermined width.

Figure 2:
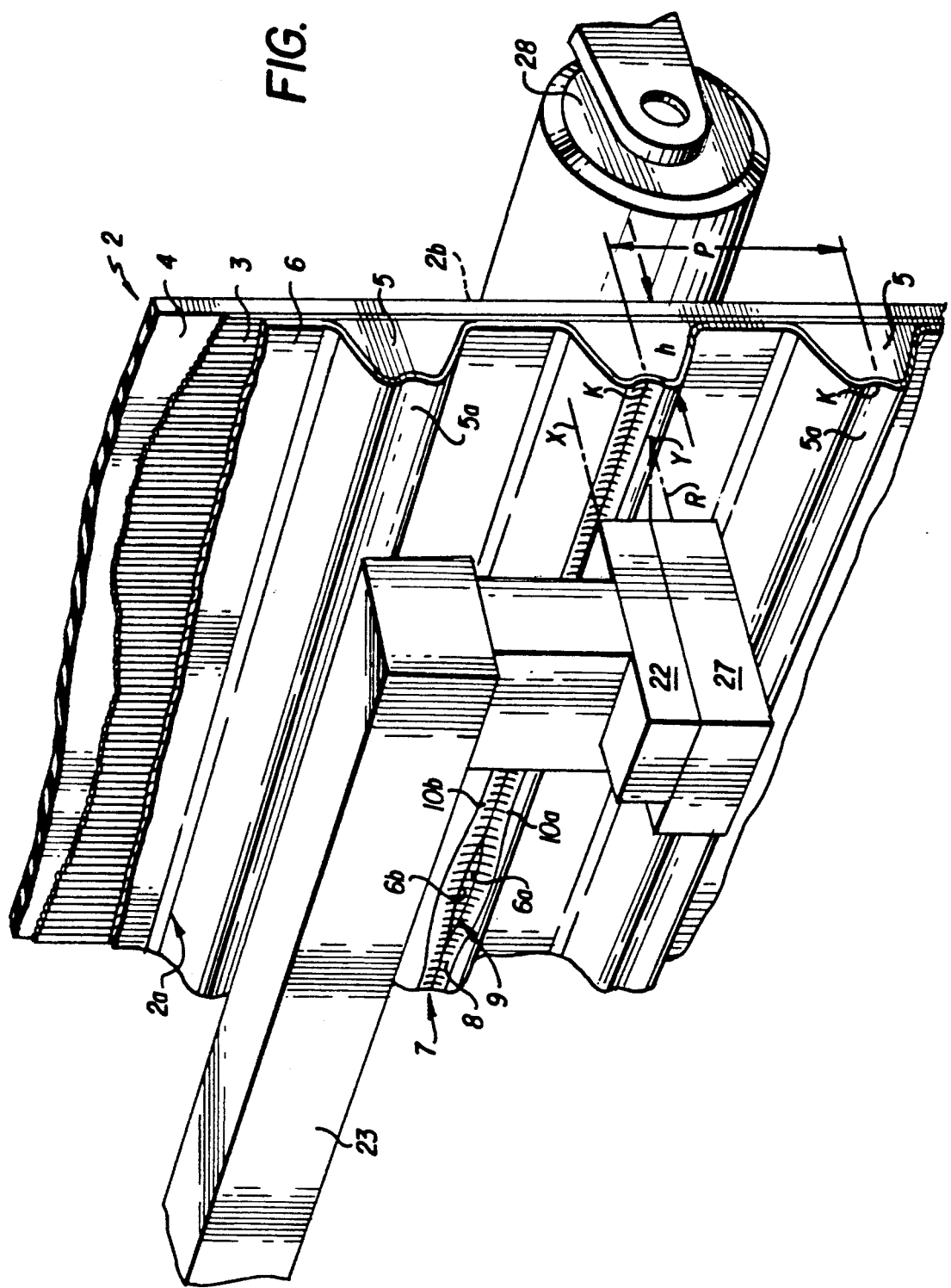
FIG. 2 is a diagrammatic perspective view of an enlarged detail of the apparatus of FIG. 1, showing a photochromatic sensor and a reading member operatively acting on the toothed surface of the sleeve.

Referring particularly to FIG. 2, each sleeve 2 substantially has at least one inextensible textile reinforcing layer 3 of substantially cylindrical configuration, embedded in at least one layer of elastomeric material 4 shaped such as to define an internal toothed surface 2a on the inner periphery of the sleeve 2.

The toothed surface 2a conventionally has a plurality of teeth 5 disposed in parallel and in side by side relation one after the other according to a predetermined pitch "P".

The configuration of teeth 5 can vary depending upon the circumstances. In the embodiment shown in the accompanying figures the teeth 5 are shaped as described in Assignee's U.S. Pat. No. 4,850,943.

Still in a known manner, applied to the toothed surface 2a is at least one lining fabric 6 which is coupled to the elastomeric material 4. The lining fabric 6 performs the double function of enhancing the resistance of the individual teeth 5 to bending stresses thereby increasing the tractive capability of the toothed belt, and protecting the elastomeric material 4 from the action of chemicals or other external agents with which the belt may be brought into contact.

The coating fabric 6 obtained by cutting to size and joining at least one fabric length, has at least a connecting junction 7 extending longitudinally to the sleeve 2 on the circumferential extension thereof. This junction 7 is essentially formed by two end edges 6a, 6b of the fabric 6 disposed close to each other and joined by a seam 8 formed with overedge stitches. In order to enable the lining fabric 6 to efficiently fulfill its functions, the absence of any faults at the junction 7 is essential.

More particularly, it is indispensable that the end edges 6a, 6b of fabric 6 do not have areas of mutual separation, of the type shown at 9 in FIG. 2, resulting for example from too strong tensionings produced on the fabric during the preceding vulcanization process carried out for the manufacture of the sleeve 2.

In addition, it may be necessary that the junction 7 and more precisely the end edges 6a, 6b of fabric 6 should be located at a predetermined point of the transverse outline of any one of the teeth 5, in order to avoid too strong stresses on junction 7 when the obtained belts are being used.

Apparatus 1 can automatically carry out the quality inspection of the junction or junctions 7 provided in a sleeve 2 by putting into practice a process that, in accordance with the present invention, essentially comprises the following steps:

a) operatively mounting the sleeve 2 on supporting and motion-imparting means;

b) moving the sleeve 2 transversely to its longitudinal axis;

c) positioning a photochromatic sensor adjacent the inner toothed surface 2a of sleeve 2, said photochromatic sensor having means to emit variable electric signals depending on the color exhibited by the toothed surface 2a at a particular reading point;

d) moving the photochromatic sensor according to a direction parallel to the sleeve 2 axis, so that said first reading point helically translates relative to the sleeve axis;

e) detecting and recording the signals emitted by the to photochromatic sensor when, due to the passage of said junction 7 past the first reading point, a mutual separation between the joined fabric end edges 6a, 6b is identified, said end edges 6a, 6b being chromatically differentiated at least from the elastomeric material layer 4;

f) detecting and recording the photochromatic sensor's position on the longitudinal extension of the sleeve 2, when a separation area between the lining fabric end edges 6a, 6b is identified at said junction 7.

In a preferred embodiment of the present process the execution of one or more preliminary steps is provided for marking the end edges 6a, 6b of fabric 6 in order to achieve the chromatic differentiation of the same from the elastomeric material 4 and the toothed surface 2a taken as a whole. In particular it is provided that at the end of the marking step also the opposite end edges 6a, 6b be chromatically differentiated from each other.

The marking step can be carried out following different modalities not of importance to the ends of the invention. By way of example, this step may be executed by applying appropriate, PVC-based for example, inks or paints along the end edges 6a, 6b of the fabric length or lengths used for the manufacture of the tubular body designed to form the toothed surface lining 6.

The application can be carried out either by hand or automatically by appropriate devices associated with the sewing machines used to make the seam or, more generally, with the apparatus adopted for making said tubular fabric bodies.

In conclusion, said marking operation causes the formation of a first marking stripe 10a and a second marking stripe 10b which are chromatically differentiated from each other along the mutually opposite end edges 6a, 6b of the lining fabric 6.

The connecting seam 8 can be advantageously made using a transparent thread in order to facilitate the inspection step described with reference to the present process.

Apparatus 1 essentially comprises a base 11 on which supporting means 12, 13, 16 designed to operatively carry the sleeve 2 are mounted. Greater details of this apparatus are given in the co-pending applications identified in the above section "Cross Reference to Related Applications".

In the embodiment shown the supporting means consists of at least one upper roller 12 rotatably engaged to the base 11 and at least one lower roller 13 parallel to the upper roller 12 and operatively engaged to a movable supporting column 14 designed to enable the lower roller 13 to move close to and apart from the upper roller 12 upon command of fluid-operated actuators 15 or similar means.

In greater detail, in the embodiment shown two upper rollers 12 and two lower rollers 13 are provided and they are disposed in parallel and in side by side relation according to substantially horizontal planes.

In addition, it is preferable that at least an auxiliary lower roller 16 disposed parallel under the lower rollers 13 should be connected to the supporting column 14.

The auxiliary roller 16 can be used in place of the lower rollers 13 when the sleeves 2 being worked have an unusually long circumferential extension.

Associated with the supporting means 12, 13, 14 is first motion-imparting means comprised of at least a first motor 17 acting on at least one of the upper rollers 12 to impart a continuous movement to the sleeve 2 in a direction substantially at right angles to the longitudinal extension of the teeth 5 provided thereon.

As shown in FIG. 1, each of the supporting rollers 12, 13, 14 is provided with a coating layer of elastomeric material 12b, 13b, 16b so that a sure grip on the toothed surface 2a may be ensured, as well as an easy adaptation to the different types of sleeves 2 being worked.

At least one of the ends 12a of each upper roller 12 can be operatively engaged to one removable support 18 slidably guide with respect to the base 11 and sideways movable apart from the upper rollers, as shown by the arrows in FIG. 1 upon command of fluid-operated cylinders 19 and 19A or the like, in order to enable the insertion of a sleeve 2 onto said upper rollers, as clearly shown in FIG. 1.

Likewise, at least one of the ends 13a, 16a of each of the lower rollers 13 and auxiliary roller 16 can be operatively engaged by a second removable support 20, connected to a side extension 14a of the supporting column 14 and sideways movable apart from the lower rollers upon command of respective actuators 21 and 21A as indicated by the arrows in FIG. 1.

Advantageously, the apparatus 1 is provided with at least a photochromatic sensor 22, arranged to act on the toothed surface 2a at a first reading point "X" (see FIG. 2) thereof so as to enable, as more clearly explained in the following, the identification of possible separation areas 9 between the end edges 6a, 6b of the fabric 6, as well as the recognition of the position of said edges on the transverse outline of the toothed surface 2a.

The photochromatic sensor 22 is not described in detail as it is known per se. In this connection please refer to publication PEC-85-9291, printed in Japan on behalf of Matsushita Electric Works, Ltd.

The photochromatic sensor 22 is fastened to a telescopically extensible bar 23, extending within the sleeve 2 parallel to the axes of the supporting rollers 12, 13, 16 upon command of second motion- imparting means consisting, for example, of at least a threaded bar not shown as known per se and conventional, driven in rotation by a second motor 24 (see FIG. 1).

The cooperation between the second motor 24 and said threaded bar gives a translational continuous motion to the photochromatic sensor 22 in a direction parallel to the axis of sleeve 2 and therefore to the longitudinal extension of teeth 5.

Preferably the photochromatic sensor 22 is so positioned that its distance from the toothed surface 2a is about 8 mm.

If necessary, a light source not shown as not of importance to the ends of the invention may also be combined with the photochromatic sensor 22, which source is adapted to illuminate the toothed surface 2a by an intensity on the order of 1,000 lux, at least at the first reading point "X".

In a known manner, the photochromatic sensor 22 is capable of emitting variable electric signals depending on the coloring exhibited by the toothed surface 2a at the first reading point "X". In this way the passage of the end edges 6a, 6b of the lining fabric 6, by virtue of the presence of the marking stripes 10a, 10b, gives rise to a variation in the electric signal emitted by the photochromatic sensor 22.

Figure 4:
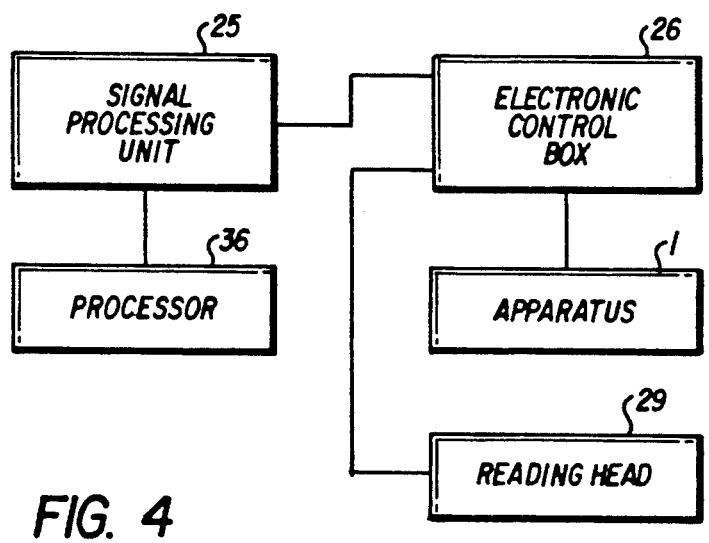
FIG. 4 is a block diagram showing the operating principle on which the apparatus of the invention is based.

The photochromatic sensor 22 is connected to an electronic processing unit 25 upon interposition therebetween of an electronic control box 26 (FIG. 4) of the type commonly referred to as a PLC, which controls the sequential operation of the various members associated with the apparatus 1 (motors 17, 18, actuator cylinders 15, 19, 21 and so on).

The processing unit 25, preferably consisting of a conventional "personal computer", carries out the processing of the signals received from the photochromatic sensor 22 for the inspection of the junction or junctions 7, in accordance with the modalities set forth in the following.

In a preferred embodiment, at least a reading member 27 preferably of the laser beam type is associated with the photochromatic sensor 22 and this member too is fastened to one end of the telescopic bar 23.

The reading member 27, not described in detail as known per se, sends a light beam "R" onto the toothed surface 2a of the sleeve 2 and, picking up the reflected light from the surface 2a struck at a second reading point "Y" adjacent the first reading point "X", is capable of emitting electric signals correlated to the distance between the reading member and the second reading point "Y" struck by the light beam "R". A freely rotating locating roller 28 disposed parallel to the movement direction of the reading member 27, acts on an outer surface 2b of the sleeve 2 to keep said surface spaced apart by a predetermined distance from the reading member.

Preferably, within the general operation of apparatus 1, the reading member 27 which is also connected to the electronic processing unit 25 upon interposition of the electronic control box 26, is used to inspect the geometrical configuration of the toothed surface 2a in accordance with a process being the object of a copending patent application filed in the name of the same applicant as identified in the above section "Cross Reference to Related Applications".

For the purpose, the processing unit 25 carries out the processing of the signals received from the reading member 27 in order to draw data relative to the geometrical configuration of the toothed surface 2a which are then compared with theoretical geometric parameters previously recorded in the processing unit itself.

Still in accordance with another copending patent application filed by the same applicant and identified above, it is also provided that the reading member 27 should also cooperate with a member emitting and receiving ultrasonic waves, operating through the sleeve 2 at a further reading point.

This transceiver member not shown as not of importance to the ends of the present invention and at all events widely described in another above identified copending patent application, is connected as well to the electronic processing unit 25 in order to identify the presence of possible structural cavities due to steam infiltrations or to the formation of gaseous substances in the elastomeric material 4 during the vulcanization process.

As regards the cooperation with the photochromatic sensor 22 provided in the apparatus of the invention, the reading member 27 is used to enable the electronic processing unit 25 to know the position of the first reading point "X" on the toothed surface outline, instant by instant.

In this way the processing unit 25 has the possibility of identifying the exact position of the end edges 6a, 6b on the extension outline of the toothed surface 2a in order to inspect whether the junction 7 has a predetermined positioning.

Input to the memory of the processing unit 25 are the theoretical geometric parameters corresponding to different types of sleeve 2 produced in the factory in which the apparatus 1 is installed. An individual code is given to the theoretical geometric parameters of each type of sleeve 2, adapted to enable the immediate selective recall thereof when the operating steps of apparatus 1 are being carried out.

The individual code corresponding to the sleeve 2 being tested is in fact detected by the electronic control box 26 when the sleeve is fitted on rollers 12, 13. To this end it is conveniently provided that the electronic control box 26 be interlocked to a magnetic reading and recording head 29 (see FIG. 1) arranged to detect recorded information on a magnetic card 30 associated with a handling support 31 conventionally used to carry the sleeves 2 and the subsequently produced belts between the various work stations in the factory. The handling support 31 is operatively engaged along a roller-bed 35 mounted in the lower part of the apparatus base 11, in order to fit the sleeve 2 onto the rollers 12, 13 which are disposed close to each other while simultaneously bringing the magnetic card 30 under the reading head 29.

Under this situation the electronic control box 26 can transmit the individual code stored in the magnetic card 30 carried by the handling support 31 to the processing unit 25.

The sleeve 2 is laid down on the upper rollers 12, for example by lowering the roller-bed 35, and afterwards the handling support 31 is slipped off the sleeve, as shown in FIG. 1, so that the removable supports 18, 20 can operatively be engaged with the ends 12a, 13a, 16a of the upper 12 and lower 6, 16 rollers.

Meanwhile, the processing unit 25 has received in its memory the theoretical geometric parameters corresponding to the individual signalled code. Therefore the processing unit 25 through the electronic control box 26 operates the lowering of the lower rollers 13, 16 to an extent sufficient to produce a given tensioning of the sleeve 2.

At this point, the apparatus 1 starts inspecting the junction or junctions 7 in the sleeve 2, in accordance with the following modalities based on the present process.

The processing unit 25 enables the electronic control box 26 to activate the first motor 17 that, through the upper rollers 12, causes rotary movement of the sleeve 2 transversely to the extension of teeth 5.

Simultaneously, the second motor 24 is activated as well, and it causes the simultaneous translation of the photochromatic sensor 22 and reading member 27 in a direction substantially parallel to the longitudinal extension of teeth 5, at a predetermined speed.

Preferably the starting point for the displacement of the photochromatic sensor 22 and the reading member 27 is sideways starting from the end of the sleeve 2, so [hat the displacement speeds of the sleeve, the sensor and the reading member are stabilized before the actual beginning of the process for the inspection of junctions 7.

Figure 3:
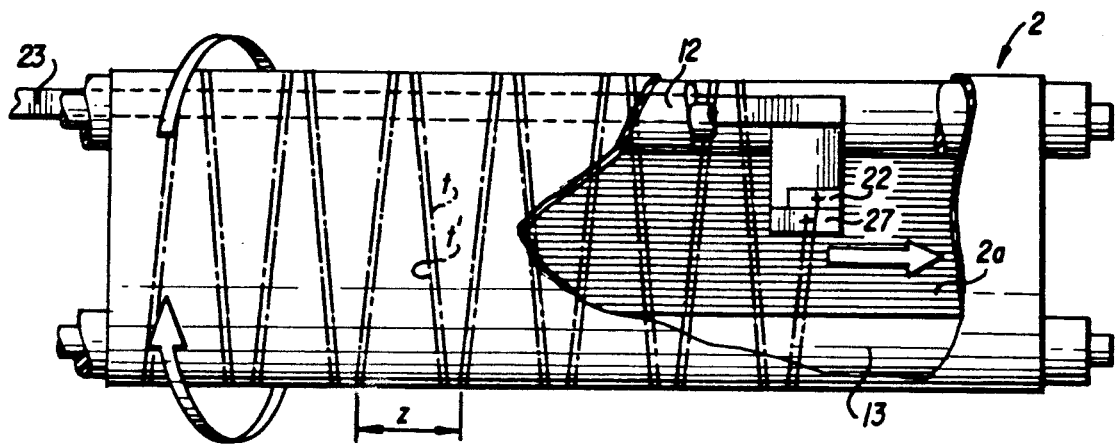
FIG. 3 is a fragmentary diagrammatic side view showing the relative movement paths taken by the photochromatic sensor and the reading member with respect to the sleeve.

When the photochromatic sensor 22 and the reading member 27 move within the sleeve 2, the first reading point "X" and the second reading point "Y" move relative to the toothed surface according to respective paths "t", "t'" which are substantially of helical form and parallel (FIG. 3), the pitch "z" of which is correlated to the ratio existing between the shifting speed of the sensor 22, the reading member 27 and the sleeve 2.

By adjusting these speeds it is possible to obtain helical paths "t", "t'" having the desired pitch "z".

The more the pitch "z" of paths "t", "t'" is reduced, the more reliable is the inspection that is carried out. A satisfactory reliability is achieved when the pitch "z" of the helical paths "t", "t'" is lower than or equal to the width of the belts to be produced.

In this manner, one can be sure that all teeth 5 belonging to each of the belts to be produced will pass in front of the reading points "X" and "Y".

As previously said, based on the electronic signals emitted by the photochromatic sensor 22 each time the junction 7 passes by the first reading point "X", the electronic processing unit 25 is capable of establishing whether the junction is correctly carried out or, on the contrary, there is a separation area between the end edges 6a, 6b in the fabric 6.

In greater detail, in the absence of a junction 7 on the first reading point "X", the photochromatic sensor 22 emits an electric signal corresponding to a black color or to any other color offered by the lining fabric 6.

When the junction 7 passes before the first reading point "X", the signal emitted by the photochromatic sensor 22 will undergo two changes, each corresponding to the color of one of the marking stripes 10a, 10b offered by the end edges 6a, 6b of fabric 6. If the signals detected by the processing unit 25 show an immediate change from the color of the first marking stripe 10a to the color of the second marking stripe 10b, it means that the end edges 6a, 6b, at least at the first reading point "X" perfectly mate with each other and therefore their junction is correct.

If, on the contrary, the signals corresponding to the colors of the two marking stripes 10a, 10b are interrupted by a short signal corresponding to the black color, it means that the end edges 6a, 6b of fabric 6 have an area of mutual separation 9 the presence of which has caused the reading of the color of the underlying elastomeric material 4 by the photochromatic sensor 22.

In this case the processing unit 25 will identify which of the belts to be produced during the following circumferential slitting operation of the sleeve 2 is going to have a faulty junction area 9.

To this end, the processing unit 25 is arranged so as to time the interval elapsing from the moment at which the photochromatic sensor 2 moved by the telescopic bar 23 has reached its operating condition before the toothed surface 2a, to the moment at which the detection of the separation area 9 between the end edges 6a, 6b has occurred.

Based on the movement speed of the photochromatic sensor 22, the processing unit 25 is therefore capable of establishing the exact position of the separation area 9 on the longitudinal extension of the sleeve 2 and, knowing the width of the individual belts to be produced, is also capable of establishing on which of said belts the found fault will be present.

As previously said, simultaneously with the above operations the processing unit 25 also detects the position of the first reading point "X" on the outline of each tooth 5 in order to check the correct positioning of the junction 7.

In greater detail the processing unit 25 identifies, based on the signals from the reading member 27, the pattern of the transverse outline of the toothed surface 2a by repeated detections of the height "h" exhibited, instant by instant, by the toothed surface at the second reading point "Y".

Simultaneously, the processing unit 25, times the interval elapsing between the different value detections of the height "h".

The processing unit 25 also carries out the identification of the passage under the second reading point "Y"

of two identical characteristic spots "K" each belonging to the transverse outline of one of the teeth 5.

These characteristic spots "K" each defined in the example described by a recess 5a formed on top of the respective tooth 5 and having a predetermined height, are unmistakably spaced apart from each other by a known amount previously stored in the processing unit 25, preferably equal to the pitch "P" of teeth 5.

By timing the interval intervening in the passage of the two characteristic spots "K", the processing unit 25 is capable of establishing the displacement speed of the toothed surface 2a relative to the reading points "X" and "Y" expressed as space/time ratio as a result of the division of the value of pitch "P" by the value of the interval of time.

Depending upon the value of the issued space/time ratio, the processing unit 25 gives a corresponding distance value from one of the characteristic spots "K" to each height "h" value detected in the course of the repeated reading steps based upon the time intervening between the detection of the height value and the detection of the passage of said characteristic point "K".

For the achievement of a greater certainty, the timekeeping of the interval of time intervening in the passage of the characteristic spots "K" should be repeated at least twice consecutively, each time referred to two different teeth 5 until the processing unit 25 finds a constant time value between a measuring and the following one for a predetermined number of times.

At the beginning of the test, the execution of these operating steps involves a temporary disenabling of the photochromatic sensor 22 and as a result there is no inspection on the first teeth 5 passing under the first reading point "X".

This lack of control however is not a problem because the unchecked teeth undoubtedly belong to one of the end belts in the sleeve 2 which, as is known, are discarded "a priori".

It is also provided that the operating steps for the detection of the space/time ratio be executed several times at predetermined intervals during the inspection test on the sleeve 2.

In this manner one can be sure that the test results are not impaired by possible variations in the relative speed between the toothed belt 2a and the reading points "X" and "Y" caused for example by uncontrolled variations in the operating speed of the first and/or second motor 17, 24, slight elastic deformations in the sleeve 2 and/or in the elastomeric coating layers disposed on rollers 12, 13, 16, or by an imperfect parallelism between the individual teeth 5 and the movement direction of the photochromatic sensor 22 and the reading member 27.

By mathematically interpolating the possible center distance existing between the first and second reading points "X", "Y", the processing unit 25 is capable of recognizing the exact instantaneous position of the first reading point with respect to the outline of the toothing 2a while the test is being carried out.

In particular, the processing unit 25 carries out the identification of the position occupied by the first reading point "X" relative to the corresponding tooth 5 at the moment that the photochromatic sensor 22 signals a color change between the first and second marking stripes 10a, 10b, in order to verify that this change corresponding to the position of the end edges 6a, 6b disposed close to each other takes place at a predetermined point on the transverse outline of tooth 5.

In this particular case, this point is coincident with one of the above mentioned spots "K".

Should the junction point between the end edges 6a, 6b be located intolerably apart from the predetermined point, the processing unit 25 will identify the position of this fault on the longitudinal extension of the sleeve 2 and establish which of the obtained belts has said fault, in the same manner as described with reference to the separation areas 9 between the end edges 6a, 6b. During the test, the position of all the separation areas 9 and the areas of anomalous location of the junction 7 are stored by the electronic processing unit 25.

When, at the end of the test, the handling support 31 is engaged again on the roller bed 35 for picking up a sleeve 2, the processing unit 25 will send signals relating to the position of the fault in the junction 7 to the magnetic card 30, through the electronic control box 26.

Signals input to the magnetic card 30 will allow other automatic machines used later in the belt production cycle to identify and discard the belts that, according to the subsequent slitting operation carried out on the sleeve 2, have a defective junction 7.

Advantageously, the process of the invention also permits a timely intervention for eliminating the causes that have resulted in the formation of faults in junction 7.

To this end, the processing unit 25 must be able to transmit data detected during the test to a processor 36.

The processor 36 performing the function of overseeing the operation of the main equipment used in the belt production cycle, will signal the improper operation of the equipment from which the formation of faults in the junction 7 is supposed to have arisen. The present invention attains the intended purposes.

The present process and apparatus allow the possible presence of mutual separation areas between the end edges of the lining fabric at the junctions to be identified in a very efficient and reliable manner, as well as anomalous positionings of the junctions on the outline of the toothed surface in the sleeve.

This process and apparatus also enable suitable and timely interventions on the machines and/or the production processes responsible for the faults found in the lining fabric junctions.

It is obviously understood that the invention as conceived is susceptible of many modifications and variations, also depending upon the type of sleeve being worked, without departing from the scope of the inventive idea as defined by the following claims.

We claim:

1. A process for inspecting junctions in sleeve lining fabrics for the manufacture of driving belts, each sleeve having a substantially cylindrical textile reinforcing layer embedded in at least a layer of elastomeric material so shaped as to define, in said sleeve, an inner toothed surface provided with a plurality of shaped teeth extending parallel to the axis of the sleeve and spaced apart from each other by a predetermined pitch P, a lining fabric being applied to said toothed surface which lining has at least two end edges joined by a seam or junction extending longitudinally to the sleeve, said process comprising the following steps:

a) operatively mounting the sleeve on supporting and motion-imparting means;
   b) moving the sleeve transversely to its longitudinal axis;
   c) positioning a photochromatic sensor adjacent the inner toothed surface of the sleeve, said photochromatic sensor being arranged to emit variable electric signals depending on the color exhibited by the toothed surface at one reading point X;

d) moving the photochromatic sensor according to a direction parallel to the sleeve axis, so that sad first reading point X helically translates relative to the sleeve axis;

e) detecting and recording the signals emitted by the photochromatic sensor when, due to the passage of said junction before the first reading point X, a mutual separation between the joined fabric end edges is identified, said end edges being chromatically differentiated at least from the elastomeric material layer;

f) detecting and recording the position of the photochromatic sensor on the longitudinal extension of the sleeve, when a separation area between the lining end edges is identified at said junction.

2. A process according to claim 1 comprising at least a preliminary step for marking the en of the lining fabric in order to chromatically differentiate the end edges from the elastomeric material layer and said lining fabric, said marking step being carried out directly oh the lining fabric, before the fabric is used for the manufacture of the sleeve.

3. A process according to claim 2 in which in the marking step two different colorings are given to the fabric end edges which are disposed close to each other.

4. A process according to claim 3 in which in the step c) the positioning of a reading member in operating condition on the toothed surface of the sleeve is also provided, the following further steps being also executed during the steps b) and d):

g) repeatedly reading the height h of the toothed surface passing under the second reading point Y in order to identify the transverse extension outline of the individual teeth;

h) timing the interval elapsing between the different value detections of the height h carried out during the repeated reading step;

i) identifying the passing under the second reading point Y of at least two characteristic spots K each belonging to the transverse outline of one of said teeth said characteristic spots K being spaced apart from each other by a known predetermined amount;

j) timing the interval intervening in the passing of said characteristic spots K under the second reading point Y, and correlating a displacement of the too surface equal to said known amount of said time interval;

k) giving to each height h value detected the course of step g), a corresponding distance from one of said characteristic spots K based on the time elapsing between the detection of height h value and the d of the passage of said characteristic spot K, as well based on the value of the space/time ratio issuing from i);

l) identifying the position of the joined end edges on the outline of the toothed surface;

m) detecting and storing the position the photochromatic sensor on the longitudinal extension the sleeve, when the joined end edges exhibit an anomalous positioning on the outline of the toothed surface.

5. A process according to claim 1 in which step f) is carried out by timing the interval elapsing between the beginning of steps c) and d) and the instant at which an area of mutual separation between the end edges is identified, said photochromatic sensor being displaced to a predetermined speed.

6. A process according to claim 4 in which step m) is carried out by timing the interval intervening between the beginning of steps c) and d) and the instant at which an anomalous positioning of the end edges disposed close to each other on the outline of the toothed surface is identified said photochromatic sensor and reading member being displaced to a predetermined speed.

7. A process according to claim 4 which said steps i) identifying the passage of two spots K and j) timing the interval intervening in the passage of said spots K are carried out several consecutive times as far as the detected interval of time is the same for a predetermined number of consecutive timings.

8. A process according to claim 4 in which said known amount according to which the characteristic spots K are spaced apart from each other corresponds to the distribution pitch P of the teeth.

9. An apparatus for the inspection of junctions in sleeve lining fabrics for the manufacture of toothed belts, each sleeve having a substantially cylindrical textile reinforcing layer embedded in at least a layer of elastomeric material so shaped as to define, in said sleeve, an inner toothed surface provided with a number of shaped teeth extending parallel to the axis of the sleeve and spaced apart from each other by predetermined pitch P, a lining fabric being applied to said toothed surface, which lining has at least two end edges joined by a seam or junction extending longitudinally to the sleeve, comprising:

supporting means arranged to operatively engage the sleeve;

first motion-imparting means cooperating with said supporting means to impart a continuous movement to the sleeve in a direction transverse to its longitudinal extension;

at least one photochromatic sensor positioned adjacent the toothed surface and having means to emit variable electric signals depending upon the color exhibited by the toothed surface at one reading point X; second motion-imparting means acting on the photochromatic sensor to impart a translation motion to the sensor in a direction parallel to the sleeve axis, so that the first reading point X translates helically to the sleeve axis;

an electronic processing unit operatively connected to the photochromatic sensor in order to identify the presence of mutual separation areas between said end edges as well as to the second motion-imparting means in order to identify the location of said separation areas on the longitudinal extension of the sleeve, said end edges being chromatically differentiated at least from said elastomeric layer.

10. An apparatus according to claim 9 further comprising at least a reading member engaged with said second motion-imparting means and arranged to act before the toothed surface in order to identify the side extension outline of the individual teeth by the repeated reading of the height h of the toothed surface itself translating before a second reading point Y, said electronic processing unit being arranged to identify the positioning of said end edges on the toothed surface outline, as well as to identify and store the position of the first reading point X on the longitudinal extension of the sleeve when said end edges as sewn together have an anomalous positioning on the toothed surface profile, said end edges being chromatically differentiated from each other.

11. An apparatus according to claim 9 in which said support means comprises at least one upper roller and at least one lower roller parallel to each other and designed to be selectively positioned close to and spaced apart from each other in order to operatively engage the sleeve giving it a predetermined tensioning.

12. An apparatus according to claim 11 in which each supporting roller has a coating layer made of elastomeric material.

13. An apparatus according to claim 9 comprising a pair of upper rollers and a pair of lower rollers disposed parallel in side by side relation according to respective horizontal planes.

14. An apparatus according to claim 11 further comprising at least an auxiliary lower roller located under said lower roller.

15. An apparatus according to claim 11 in which said lower roller is operatively engaged to a supporting column movable upon command of actuator means to enable the lower roller to move close to and away from the upper roller.

16. An apparatus according to claim 11 in which each of said upper and lower rollers has at least one of its ends operatively supported by a removable support movable away sideways from the respective roller in order to enable the engagement of the tubular sleeve on said upper and lower rollers.

17. An apparatus according to claim 10 further comprising at least a freely rotating locating roller disclosed parallel to the displacement direction of the reading member and acting on an outer surface of the sleeve so as to keep said surface to a predetermined distance from the reading member.

18. An apparatus according to claim 9 further comprising a magnetic reading and recording head operatively connected to said electronic processing unit to transmit an individual stored code to said unit on a magnetic card associated with a handling support carrying the sleeve being worked on the supporting rollers, in said processing unit and on said magnetic card there is stored the geometrical parameters of several sleeves which can be selectively recalled through said individual codes.

19. An apparatus according to claim 9 in which said electronic processing unit is operatively connected to a processor in order to transmit to the latter the presence of separation areas between the end edges and of anomalous positionings of the end edges on the outline of the toothed surface, said processor being arranged to consequently signal operating anomalies in equipment previously used for the manufacture of the sleeve.

20. An apparatus according to claim 18 in which said processing unit is arranged to record on the magnetic card the position of said separation areas on the longitudinal extension of the sleeve and of the anomalous positionings of the end edges sewn together on the toothed surface outline, through the magnetic reading and recording head .

21. An apparatus according to claim 18 in which said head and card are of the magnetic type.

22. A process for inspecting junctions in sleeve lining fabrics for the manufacture of driving belts, said fabric being positioned between two opposite first and second boundary surfaces of the sleeve, each sleeve having a substantially cylindrical textile reinforcing layer embedded in at least one layer of elastomeric material so shaped as to define, in said sleeve, one of said two boundary first and second surfaces, on the first of said boundary surface there being applied a lining fabric having at least two end edges connected by junction extending longitudinally to the sleeve, said process comprising the following steps:
  a) operatively mounting the sleeve on supporting and motion-imparting means;
  b) moving the sleeve transversely to its longitudinal axis;
  c) positioning a photochromatic sensor adjacent said first boundary surface on the sleeve, said photochromatic sensor having means to emit variable electric signals depending on the color exhibited by said surface at a first reading point X;
  d) displacing the photochromatic sensor along a direction parallel to the sleeve axis, so that said first reading point X helically translates relative to the sleeve axis;
  e) detecting and storing the signals emitted by the photochromatic sensor when, following the passage of said junction before the first reading point X, a mutual separation between the fabric end edges sewn together is identified, said end edges being chromatically differentiated at least from the elastomeric material layer;
  f) detecting and storing the position of the photochromatic sensor on the longitudinal extension of the sleeve, when a separation area is identified between the end edges of the lining fabric at said junction.

* * * * *